United States Patent [19]
Bowman

[11] Patent Number: 5,491,285
[45] Date of Patent: Feb. 13, 1996

[54] PHYTOPHTHORA RESISTANCE GENE OF CATHARANTHUS AND ITS USE

[75] Inventor: Robert N. Bowman, Gilroy, Calif.

[73] Assignee: Goldsmith Seeds Inc., Gilroy, Calif.

[21] Appl. No.: 184,319

[22] Filed: Jan. 21, 1994

[51] Int. Cl.$^6$ .............................. A01H 1/04; A01H 4/00; A01H 5/12; A01H 5/00; A01H 5/10

[52] U.S. Cl. ........................ 800/200; 800/250; 800/255; 800/DIG. 67; 435/240.4; 435/240.48; 435/240.49; Plt./54.1; 47/58

[58] Field of Search .................................. 800/200, 205, 800/250, 255, DIG. 67; 935/1, 52; 435/240.1, 240.4, 240.48, 240.49, 240.5; 536/23.6; Plt./54.1; 47/58

[56] References Cited

PUBLICATIONS

Ferrin, D. M. et al., "Population Dynamics of *Phytophthora parasitica*, the Cause of Root and Crown Rot of *Cathranthus roseus*, in Relation to Fungicid Use"; *Plant Disease*, Jan., 1992.

Chase, Ann et al., "Is Your Vinca Resistant to Phytophthora?", *Grower Talks*, Aug., 1993.

Chockalingam, S. et al., "Impact of the Extract of *Cathranthus roseus* on Feeding and Enzymatic Digestive Activities of *Spodoptera–litura*", *J. Environmental Biology*, 1989.

Colon, L. T. et al., "Resistance to potato late blight (*Phytophthora infestans* (Mont.) de Bary) in *Solanum nigrum*, *S. villosum* and their sexual hybrids with *S. tuberosum* and *S. demissum*", *Euphytica*, 66:55–64, 1993.

Reifschneider, F. J. B. et al., "Inheritance of adult–plant resistance to Phytophthora capsici in pepper", *Euphytica*, 62:45–49, 1992.

Bartual, R. et al., "Gene action in the resistance of peppers (*Capsicum annuum*) to Phytophthora stem blight (*Phytophthora capsici* L.)", *Euphytica*, 54:195–200, 1991.

Sevestre–Riigouzzo, M. et al., "Genetic diversity and alkaloid production in *Catharanthus roseus*, *C. trichophyllus* and their hybrids", *Euphytica*, 66:151–159, 1993.

Roller. 1978. In Production of Natural Compounds by Cell Culture Methods. Proc. Int. Symp. Plant Cell Culture. Alfermann et. al., eds. pp. 95–104, München, FRG.

Arens et al. 1978. Planta medica. 34:37–46.

Patra. 1982. Science and Culture. 48(6): 217–218.

Levy et al. 1983. Euphytica. 32: 557–564.

Schubert et al. 1986. Phytopathology. 76(10): 1071.

Vitti et al. 1985. Hort Science. 20(2): 186.

Potrykus. 1991. Annu. Rev. Plant Physiol. Plant Mol. Biol. 42:205–225.

Finnegan et al. 1994. Bio/Technology 12: 883–888.

Songstad. 1990. Plant Physiol. 94:1410–1413.

Umaerus et al. 1983. In Phytophthora. Erwin et al., eds. The American Phytopathological Society.

*Primary Examiner*—David T. Fox
*Assistant Examiner*—Erich E. Veitenheimer
*Attorney, Agent, or Firm*—Henderson & Sturm

[57] ABSTRACT

The present invention relates to a disease resistant Catharanthus seed, Catharanthus plant, Catharanthus variety and Catharanthus hybrid. More specifically, the invention relates to a Catharanthus plant having resistance to the fungal disease Phytophthorao. The invention also relates to an increased level of resistance to aphids and other pests and an increased level of total alkaloid content. The invention further relates to the method of crossing Catharanthus plants containing the resistance to Phytophthora to produce disease resistance and increased total alkaloid level in Catharanthus plants and in other crop plants.

38 Claims, 1 Drawing Sheet

PHYTOPHTHORA RESISTANCE GENE OF CATHARANTHUS AND ITS USE

BACKGROUND OF THE INVENTION

The present invention relates to a Catharanthus seed, a Catharanthus plant, a Catharanthus variety and a Catharanthus hybrid which contain a level of resistance to the disease *Phytophthora parasitica*. The present invention also relates to a Catharanthus plant product, an increased level of alkaloid content, and an increased resistance to certain insects.

*Catharanthus roseus* (L.) G. Don, also called periwinkle, or vinca, originates from Madagascar and belongs to the family of the Apocynaceae. This species is frequently grown annually from seed or cuttings in temperate climates for use in summer bedding or as a pot plant for the conservatory or the windowsill. *C. roseus* has long been grown as an ornamental in tropical regions of the world. As a consequence of its self-seediness (ability to pollinate itself and readily form mature selfed seed) it is now widely naturalized in many tropical regions. Commonly known as Madagascar periwinkle or vinca (not to be confused with the separate genus Vinca) this ornamental is commonly propagated from seed and less frequently from stem cuttings.

Periwinkle is valued for its bushy habit, large desirable flowers, tolerance to heat, drought and direct sunlight. In addition to its horticultural merits, *C. roseus* contains alkaloids used to retard certain diseases, such as leukemia.

Catharanthus species are well known for their production of indole alkaloids as described in Farnsworth, *Lloydia* 24:105–139 (1961); Sevestre-Rigouzzo, et al., *Euphytica* 66:151–1569 (1993). *Catharanthus roseus* is one of the most thoroughly investigated of plants with regard to its constituent indole alkaloids, of which more than 70 have been isolated from the whole plant as described in Balsevich and Hogge, *J. Nat. Prod.*, 51: 1173–1177 (1988). Alkaloids are generally known as compounds biologically active against pathogens and herbivores as discussed in vanDam, et at., *Oecologia* 95:425–430 (1993). Indole alkaloids are potent antifeedants. Tested in a bio-assay using a 0.04% solution, vinblastine and catharanthine appeared to be the most deterrent alkaloids against the polyphagous Spodoptera larvae as described in Meisner, et al., *J. Econ. Entomol.* 74:131–135 (1981); Chockalingam, et at., *J. Environ. Biol.* 10:303–307 (1989). Periwinkle extracts have also been shown to have strong inhibitory activity against several bacterial genera. Farnsworth *Lloydia* 24:105–139 (1961) also described the anthelmintic activity of alkaloid fractions of *C. roseus*. Alkaloids obtained from C. roseus provide the basis of a 22-year old industry yielding well over a hundred million dollars annually as described in Raven, *Diversity* 9:49–51 (1993). The anticancer activity of vinblastine and vincristine, both isolated from *C. roseus*, is well documented in the pharmaceutical industry.

To date there has been no known resistance to Phytophthora in Catharanthus species. The principle problem with growing periwinkle is its sensitivity and susceptibility to attack by *Phytophthora parasitica*. Stem and crown rot caused by *Phytophthora parasitica* is a common problem on Catharanthus. Symptoms typically are associated with the final stages of disease development, but infected plants can support a population of the pathogen without showing visual symptoms.

Keen and Yoshikawa (in Phytophthora, Erwin et al., eds, 1983) 279–284 describe natural mechanisms of resistance to Phytophthora spp. in other crops. General resistance mechanisms against Phytophthora spp. include structural features of the host, preformed chemical inhibitors, induced structural barriers, hypersensitive reactions and phytoalexins. Keen, *Adv. Plant Pathol.* 65:35–82 (1982) also suggests that specific resistance to Phytophthora spp. is usually controlled by single host resistance genes. Monogenetically inherited resistance to different species of Phytophthora has been reported in several crops other than Catharanthus. Resistance has most often been found to be attributable to single, dominant alleles (Umaerus et al., in Phytophtohra, Erwin et al., eds 1983) 315–326. Colon et al., *Euphytica*. 66:55–64 (1983) described resistance to *Phytophthora infestans* in Solanum spp.

The chemical metalaxyl (which is the active ingredient of the eumycete-specific fungicities Subdue and Ridomil) has been the primary fungicide used by nursery personnel to control stem and crown rots caused by Phytophthora spp. as discussed in Ferrin, et al. *Plant Disease*, Vol. 76, p. 60–63, p. 82–84 (1992). While some control of the diseases is effected by the chemical metalaxyl, Ferrin, supra has found one isolate of *P. parasitica* from a southern California nursery which was insensitive to metalaxyl. Tolerance to metalaxyl was expressed in vivo by the isolate chosen by Ferrin, et al. supra. Furthermore, this metalaxyl-tolerant isolate appears to be as virulent as sensitive wild-type isolates. For nurseries where plants are grown in containers, widespread failures in disease control would not necessarily be expected immediately after the appearance of metalaxyl tolerance because of the low frequency with which such tolerance appears and the time needed for the pathogen population to increase and be dispersed. Widespread disease control failures occur only after a large part of the pathogen population has become tolerant to the pesticide. The rate at which this metalaxyl-tolerant population becomes established depends largely on the stability of the pesticide tolerance, the selection pressure exerted on the pathogen population, and the ability of the pathogen to disperse. Because species of Phytophthora and Pythium have been detected in recycled irrigation water in nurseries in California, the requirement that commercial nurseries in certain areas of California trap and recycle all runoff water greatly increases the risk of recycling fungicide-tolerant populations of these pathogens in those nurseries. Thus, the appearance of metalaxyl tolerance could eventually result in control failures if the treatment of recirculated water is not sufficient to eliminate propagules of Phytophthora spp. and the selection pressure due to the continued use of the fungicide metalaxyl is maintained.

The continuous use of metalaxyl as the primary means of controlling diseases caused by Phytophthora increases the likelihood for the development of insensitivity to metalaxyl (Ferrin et al., supra). History has shown new isolates of *P. parasitica* insensitive to new fungicides eventually will evolve and since the use of chemicals can have side effects on people using the chemicals and the environment, it is highly desirable to use a *Catharanthus roseus* having genetic resistance to Phytophthora spp.

A genetic resistance to Phytophthora in periwinkle, if available, could be used to reduce or eliminate the use of the chemical metalaxyl and result in increased cost efficiencies and environmental safety.

SUMMARY OF THE INVENTION

The present invention relates to a Catharanthus seed, a Catharanthus plant, a Catharanthus variety, a Catharanthus hybrid and a method for producing a Catharanthus plant.

More specifically, the invention relates to a Catharanthus plant having resistance to the fungal disease *Phytophthora parasitica*. The present invention also relates to a Catharanthus plant having a moderate to high level of resistance to aphids (*Myzus persicae*) and mites (*Tetranychus urticae*), and a Catharanthus plant having an increase in total alkaloid content.

The present invention further relates to a method of producing the disclosed Catharanthus plants and seeds by crossing a Phytophthora resistant plant of the instant invention with another Catharanthus plant. The invention also relates to the transfer of the genetic Phytophthora resistance into genera other than Catharanthus, including but not limited to the following genera: Solanum, Capsicum, Eucalyptus, Carica, Ananas, Fragaria, Camellia, Castanea, Persea, and Citrus.

The present invention further relates to a periwinkle plant having a level of resistance to certain insects, including but not limited to aphids (*Myzus persicae*) and mites (*Tetranychus urticae*).

The present invention further relates to a periwinkle plant which has a total alkaloid content of at least 2.0 percent or greater.

BRIEF DESCRIPTION OF THE DRAWINGS

In the accompanying drawing.

DETAILED DESCRIPTION OF THE INVENTION

Figure 1:
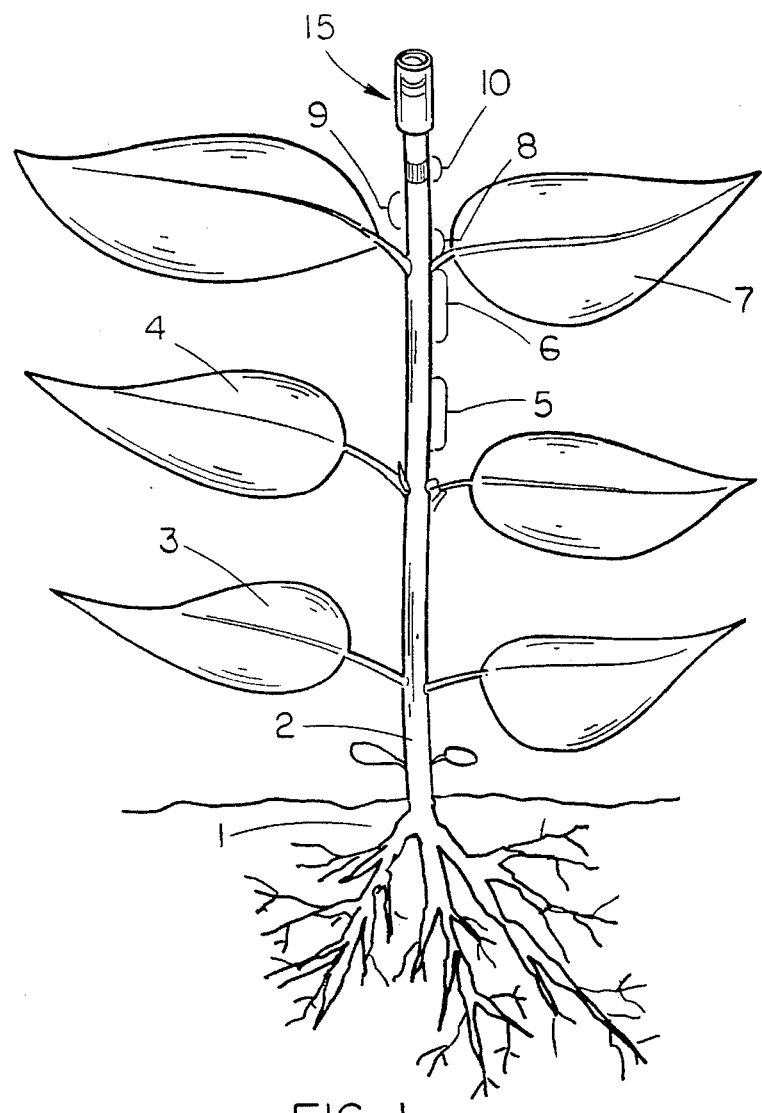
FIG. 1 is a schematic perspective view of a periwinkle plant along wherein the numbers 1–10 indicate ratings for various levels of Phytophthora resistance or sensitivity.

In order to provide an understanding of several of the terms used in the specification and claims, the following definitions are provided:

Total alkaloid content—The term 'total alkaloid content' is intended to refer to the total alkaloid content expressed as a percent of total dry weight in the plant tissue.

Homogeneous Assemblage—The term 'homogeneous assemblage' is intended to refer to a group of seeds or plants which are homogeneous for a given periwinkle characteristic. This term is intended to include any seeds or plants which are homogeneous for either of the traits of Phytophthora resistance or total alkaloid content.

Plant Product—The term 'plant product' is intended to refer to plant extracts and plant derived chemical compounds or structures including alkaloids.

*Catharanthus roseus* (L) G. Don, also called periwinkle and vinca is primarily a self-pollinating species. The *Catharanthus roseus* of the present invention reproducibly expresses resistance to *Phytophthora parasitica*. We have isolated from our breeding populations a transferrable gene which conveys resistance to Phytophthora. This disease resistance trait has been expressed in many different genetic backgrounds of periwinkle.

To date, there is no known resistance to Phytophthora in any commercial cultivar of periwinkle except for the present invention. Additionally, there are no known reports of resistance to Phytophthora in any Catharanthus species, cultivar, in the wild or commercially available. All available cultivars and naturalized collections from the U.S., Mexico, Central America, Africa and Madagascar, have been tested and no indication of Phytophthora resistance has been found as shown in Tables 1 and 2. This previously unknown disease resistance arose from breeding and research efforts which were conducted beginning in 1988.

TABLE 1

Phytophthora Resistance in Periwinkle Cultivars

| Cultivar | Resistant:Sensitive Ratio | |
|---|---|---|
| Pretty in Pink | 0:1 | (>300)[1] |
| Pretty in White | 0:1 | (>300) |
| Pretty in Rose | 0:1 | (>100) |
| Parasol | 0:1 | (>100) |
| Tropicana Rose | 0:1 | (>200) |
| Tropicana Bright Eye | 0:1 | (>200) |
| Tropicana Pink | 0:1 | (>200) |
| Tropicana Blush | 0:1 | (>200) |
| Peppermint Cooler | 0:1 | (>100) |
| Grape Cooler | 0:1 | (>100) |
| Morning mist | 0:1 | (>100) |
| Pink Panther | 0:1 | (48) |
| Sahara Madness Bright Eye | 0:1 | (48) |
| Polka Dot | 0:1 | (48) |
| Little Pinkie | 0:1 | (>300) |
| Little Bright Eye | 0:1 | (>300) |
| Little Blanche | 0:1 | (>300) |
| Little Delicata | 0:1 | (48) |
| Little Linda | 0:1 | (48) |
| Inter-variety hybrids[2] | 0:1 | (>2952) |

[1]Number in parentheses indicates number of individual plants tested.
[2]123 hybrid combinations between commercially-available cultivars and Goldsmith breeding lines not containing Phytophthora resistance. Includes line numbers 13043, 13498, 13500, 13509, 13522, 13533, 13534, 13535, 13536, 13639, 13861, 14322, 14590

TABLE 2

Phytophthora Resistance in Catharanthus spp.

| Species | Source | Resistant:Sensitive Ratio |
|---|---|---|
| *C. longifolius* | Madagascar (8408)[1] | 0:1 |
| *C. roseus* | Madagascar (8430) | 0:1 |
| | Madagascar (8440) | 0:1 |
| | Madagascar (8442) | 0:1 |
| | Madagascar (8443) | 0:1 |
| | Mexico (13635)[2] | 0:1 |
| *C. trichophyllus* | Madagascar (12914)[3] | 0:1 |

[1]Field collection number of R. N. Bowman
[2]Provided by J. Marsh
[3]Provided by A. Petit The instant invention is a genetic resistance to the disease Phytophthora in periwinkle wherein periwinkle plants which are exposed to this disease become infected but there is no spread or movement of this disease through the plant. The result is the resistant periwinkle plants stay healthy and do not die after exposure to Phytophthora. How this disease resistance gene acts by preventing the spread of the disease organism within a periwinkle plant is unknown. One possible mechanism of action is an enhanced alkaloid content within the plant.

The genetic basis for Phytophthora resistance in periwinkle seems to involve a single dominant allele. This observation parallels Phytophthora resistance observed in other crops as described in Umaerus et al. (in Phytophthora, Erwin et al., eds, 1983). Ongoing breeding trials will help to further characterize the genetic basis for Phytophthora resistance in Catharanthus. When the disease resistance gene is incorporated into different genetic backgrounds of periwinkle, the disease resistance characteristic is transferred into these genetic backgrounds.

Once true-breeding resistant lines are developed that also possess horticulturally valuable traits (ex. compact habit, desirable colors), then open pollinated resistant seed from these lines can be marketed. Also possible is the use of a true-breeding resistant line as one of the parents in $F_1$ hybrid seed production resulting in an $F_1$ hybrid which expresses Phytophthora resistance. Additionally, transferring the Phytophthora resistance gene of the present invention into crops other than Catharanthus may reduce the damage caused by Phytophthora in those crops.

As used herein, the term "plant" includes plant cells, plant protoplasts, plant cells of tissue culture from which periwinkle plants can be regenerated, plant calli, plant clumps, and plant cells that are intact in plants or parts of plants such as pollen, flowers, seeds, leaves, stems, and the like.

Tissue culture of periwinkle is described in van der Heijden et at. "Cell and Tissue Cultures of *Catharanthus roseus* (L.) G. Don: A Literature Survey", *Plant Cell, Tissue and Organ Culture* 18:231–280 (1989), incorporated herein by reference. As described in this article, the presence of the therapeutically valuable cytotoxic alkaloids resulted in Catharanthus becoming one of the major fields of interest in modern plant cell biotechnology. The low yields of these dimeric indole alkaloids (approximately 0.0005%) and the subsequent high price of them were major motives to study the possibilities for the production of these alkaloids by cell and tissue cultures. The first efforts in this tissue culture with periwinkle date from approximately 25–30 years ago. Thus, another aspect of this invention is to provide for cells which upon growth and differentiation produce the disease resistance to Phytophthora in periwinkle.

In addition to providing resistance to Phytophthora, the transfer of the dominant resistance gene to different genetic backgrounds has produced what we believe are the associated characteristics of increased total alkaloid content expressed as a percent of total dry weight in the plant and increased tolerance or resistance to certain insects, including aphids and mites. It is believed that the elevated level of total alkaloid content may be directly associated with the increased plant resistance to aphids and mites and may also be somewhat associated with the level of Phytophthora resistance. The important traits of increased total alkaloid content and insect resistance are additional objects of the present invention.

Eilert et al., as discussed in *Plant Physiol.*, 126:11 (1986); *Arch. Biochem., Biophys.*, 254:491 (1987) were able to induce alkaloid accumulation in a cell suspension culture of *C. roseus* upon treatment of the cultures with homogenates of various fungi, thus further suggesting a relationship between alkaloid production and potential fungal resistance. Nef et al., *Plant Cell Reports* 10:26–29 (1991), were also able to stimulate major alkaloid production in *Catharanthus roseus* cells with an extract of the fungus *Pythium vexans*. Finally, vanDam, et al., *Oecologia* 95:425–430 (1993) found that indole alkaloid production in *Catharanthus roseus* was not inducible by mechanical leaf damage alone. The Phytophthora resistance gene of the instant invention is strongly implicated in the modulation of alkaloid synthesis and activity in Catharanthus. This activity, however, does not preclude other possible aspects of the resistance phenomenon.

Development of the Phytophthora resistance gene in Catharanthus has provided a straightforward means of providing non-pesticide protection to an important horticultural crop. Use of the gene imparts protection from ubiquitous Phytophthora infection and may aid in protection from other fungal and insect pathogens. Additionally, the gene is both user and environment friendly by reducing or eliminating the amounts of pesticides necessary to maintain the crop. Protection from Phytophthora as well as other potential broad spectrum protection makes the resistance gene potentially valuable in other crops. The annual dollar loss from Phytophthora infections is enormous. *Phytophthora cinnarnomi*, alone, has nearly 1,000 hosts as discussed in Zentmeyer, Monogr. 10, *Am. Phytopathol. Soc.* 96 pp. (1980), many of which are important crop plants. *Phytophthora infestans*, the cause of the late blight of potatoes, which produced the great potato famine of 1846–47, resulted in the starvation of about 800,000 people. The disease is still a serious problem today. Non-pesticide reduction or elimination of Phytophthora losses would be of much significance to both food and ornamental crops. Any new source of resistance to either aerial or root Phytophthora diseases is potentially very valuable.

EXAMPLES

The following examples are provided to further illustrate the present invention and are not intended to limit the invention beyond the limitations set forth in the appended claims.

EXAMPLE 1

In Vitro Growth and Inoculation with the Phytophthora Pathogen

In vitro culture of *Phytophthora parasitica*, the causative agent of wilt in Catharanthus, is described in Gill, et at., (1977). The fungus readily grows on V-8 juice agar. Isolation and identification of strains of the fungus were accomplished by methods known to those skilled in the art. In testing for resistance to the fungus, we used the 12 different fungal isolates shown in Table 3 including pathogens obtained from commercial nurseries and plantings experiencing severe fungal attack. Isolates were obtained from Ferrin et al., as discussed in Ferrin et al., supra. Periwinkle plants were grown from seed using standard methods commonly known to those in the nursery trade. Plants were grown to the five-plus node stage (as shown in FIG. 1) before inoculation. For comparisons of pathogenicity between the Phytophthora isolates, individual periwinkle plants were cloned via stem cuttings prior to inoculations.

Figure 2A:
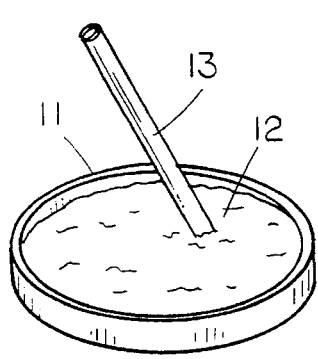
FIGS. 2A, 2B, and 2C show schematically stages of the method of inoculation of the Catharanthus plant with the Phytophthora inoculum.
Figure 2B:
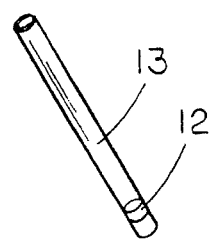
Figure 2C:
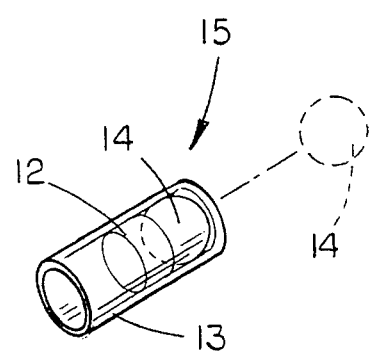

Axenic Phytophthora cultures were used to prepare inoculation capsules as shown in FIGS. 2A, 2B, and 2C. A clear plastic drinking straw (13) was used to punch agar explants (12) of the fungus from the culture dish (11). The agar explant (12) was then positioned into a short inoculation capsule (15) where a 15 mm segment of the plastic drinking straw (13) was sealed at one end with a 6 mm. diameter spherical glass bead (14). The surface of the fungal mycelium was placed away from the bead.

Periwinkle seedlings were prepared by cutting the upright stem between the fourth and fifth nodes with a clean razor blade. As shown in FIG. 1, an inoculation capsule (15) was then placed on the stem stump and gently pressed downward, thus forcing the fungal mycelium against the exposed stem surface. Controls were prepared in a similar manner, but without the fungal isolate.

The inoculated plants were then grown in a greenhouse using normal methods known to those skilled in the art. After approximately three weeks, the plants were then scored for the degree of movement of the fungus in the plant tissues,

TABLE 3

Sources of *Phytophthora parasitica* cultures[1]

| Isolate | Source |
|---|---|
| A | Premier Color Nursery, Fallbrook, CA |
| B | Premier Color Nursery, Fallbrook, CA |
| C | Premier Color Nursery, Fallbrook, CA |
| D | Premier Color Nursery, Fallbrook, CA |
| E | Premier Color Nursery, Fallbrook, CA |
| F | Premier Color Nursery, Fallbrook, CA |
| G | Premier Color Nursery, Fallbrook, CA |
| H | Summerlin Project, Summerlin Parkway, Las Vegas, NV |
| I | Summerlin Project, Summerlin Parkway, Las Vegas, NV |
| J | The Lakes Country Club, home garden, Palm Desert, CA |
| K | Color Spot Nursery, Fallbrook, CA |
| L | D. Ferrin, see Ferrin et al., 1992 |

[1]Identity of all 12 isolates as *P. parasitica* was confirmed by Dr. J. Mitchell, Department Plant Pathology, University of Florida, Gainsville.

Example 2

Assessment of Infection—Definition of Resistance

The rating scale 1–10 as described in Table 4 and schematically shown in FIG. 1 was used to measure the degree of infection and extent of movement of the pathogen through intact tissues of the inoculated plant. The degree of infection for each seedling in a family was determined as were the ratios of resistant to sensitive progeny as identified in Tables 1, 2, 5, 6 and 7. Three weeks after inoculation, the extent of tissue necrosis was assessed using the rating scale of Table 4 and FIG. 1. Plants that were able to arrest the movement of the fungus within the uppermost portion of the top internode were considered resistant; additionally, plants showing partial necrosis at the uppermost node but without continued movement below the top-most node were considered resistant if the fungus did not continue downward nearing the second node. Resistance in Catharanthus to *Phytophthora parasitica* was defined as the ability to arrest the movement of the pathogen at or near the first node below the infection site. In contrast, sensitivity was defined as the inability to arrest the movement of the pathogen ultimately resulting in death of the plant.

TABLE 4

Rating Scale for Resistance Testing
Ratings of 5–10 are considered resistant.
Ratings of 1–4 are considered sensitive or susceptible.

| Rating Scale | Description of Category |
|---|---|
| | Also: See FIG. 1 for Schematic Representation of Rating Scale |
| 10 | Clear Abscission zone formed well above uppermost node; no sign of darkening below abscission zone; abscission zone forming quickly. |
| 9 | Necrosis clearly stopped well above uppermost node; no abscission zone but no darkening (or continuation of darkening) well above uppermost node. |
| 8 | Necrosis stopped in crown at or just above uppermost node; no sign of infection in uppermost leaves. |
| 7 | One or both uppermost leaves chlorotic or clearly infected but not rapidly dying. The infecfion has been stopped at the node. |
| 6 | Infection present in uppermost portion of second internode, appearing arrested just below the top node. |
| 5 | Compared to the sensitive control plants progression of necrosis is occurring much more slowly. Necrosis arrested within the second internode, with no further movement, even after prolonged time. |
| 4 | Upper node dead, darkening of lower axils; several nodes clearly affected. No apparent arrest of the disease. |
| 3 | Two or more nodes dead; other nodes showing infection. |
| 2 | Some green in lower stem but death will occur in a few days. |
| 1 | Rapid and complete death, as in non-resistant controls. |

Example 3

Lack of Phytophthora Resistance in Existing Catharanthus Cultivars

All commercially available cultivars developed by public institutions and/or companies other than Goldsmith Seeds, Inc. were screened for Phytophthora resistance using the aforementioned methods. Results of the tests are shown in Table 1 and indicate that no commercial cultivar is resistant to Phytophthora. No commercially available cultivar is currently claimed by its manufacturer or distributor to be Phytophthora resistant. Chase and King, Grower Talks 57:63–69 (1993) have suggested that some cultivars are more susceptible to Phytophthora than others; they, however, found that all cultivars they tested were susceptible to *P. parasitica.*

Example 4

Lack of Phytophthora Resistance in Wild Catharanthus spp.

Assessions of Catharanthus spp. germplasm were also tested for Phytophthora resistance using the aforementioned methods of Examples 1 and 2. Wild germplasm of Catharanthus is difficult to obtain due to limited native distributions (Madagascar) and widespread destruction of its native habitat. Germplasm was collected in Madagascar of *C.longifolius* and *C. roseus*. Also representative germplasm of *C.trichophyllus* from Annik Petit (CNRS, Institut des Sciences Vegetales, France) was obtained. Non-resistance in these assessions is summarized in Table 2. Clearly, wild species of Catharanthus are not Phytophthora resistant.

Example 5

New Resistant Lines

As shown in Table 5, in the process of screening several hundred species x species, cultivar x species, and cultivar x cultivar Catharanthus hybrids for Phytophthora resistance in June, 1992, three experimental hybrid lines, 13516, 13517 and 13518 were identified that expressed good resistance. At that time, this resistance was the only resistance which we had ever found, despite concurrent extensive testing of all available native and naturalized collections and all existing cultivar germplasm. Further, the lines were not true breeding for resistance since they segregated both resistant and sensitive individuals as shown in Table 5. Subsequent analysis of pedigrees also shown in Table 5 suggested that the resistance may be the consequence of a single dominant (R) allele. Genetic analysis was complicated by the fact that parents in preceding generations had not been previously tested for resistance but had been discarded after the crosses were completed.

TABLE 5

Pedigree of lines 13516, 13517, and 13518, in which Phytophthora resistance was initially identified

| | | |
|---|---|---|
| 8424-3[a] × 10132-1[b] = | 11461 | |
| 11461-1[c] × SELF = | 12669 | |
| | 12669-1[c] × SELF = | 13516 (segregating for resistance[d]) |
| | 12669-3[c] × SELF = | 13517 (segregating for resistance[d]) |
| | 12669-4[c] × SELF = | 13518 (segregating for resistance[d]) |
| 11461-1[c] × 11969-12[b] = | 12825 | |
| | 12825-1[c] × SELF = | 14681 (all sensitive) |
| | 12825-2[c] × SELF = | 14680 (all sensitive) |
| 11892-5[b] × 11461-1[c] = | 12819 | |
| | 12819-1[c] × 13536-51[c] = | 14282 (all sensitive) |

[a]Field collection of R. N. Bowman, actual resistance unknown; plant was discarded after breeding crosses were made.
[b]Cultivar Pretty-In-White, not known to contain any resistance; see Table 1.
[c]Actual resistance unknown; plant was discarded after breeding crosses were made.
[d]See Tables 6-7 for continuation of these lines.

Pedigree analysis of the three lines carrying resistance (13516, 13517, 13518) indicated they shared in common a single plant (8424-3). This single plant had been considered a mutant form because of its light blue color and extreme infertility. We had never before seen the flower color in any wild species, cultivar or hybrid; further, the plant did not fit the key of any wild species as discussed in Veyret, *Catharanthus Alkaloids*, (1974). The initial motivation for using the plant in a breeding program was to capture the mutant color, remove it from its infertile background and use it for development of a new cultivar color.

Additional crossing generations were undertaken to better understand the genetic basis of the resistance geneo Example 6

Genetic Segregation of Resistance

Individual plants from line numbers 13516, 13517, and 13518 were selfed; progenies in the next generation were checked for segregation of resistance (see Table 5). Additionally, as shown in Table 6, individuals from 13516, 13517, 13518 were also outcrossed to known sensitive lines. The $F_1$ progenies from these out crosses were also assessed for resistant: sensitive ratios.

The presence of sensitive progeny in selfs of phenotypically resistant individuals confirms that resistance is controlled by a dominant allele. Segregating ratios in selfs and $F_1$ generations confirm that resistance is monogenically controlled by two alleles, (R) for Phytophthora resistant, and (r) for Phytophthora sensitive. Table 7 indicates that $F_2$ segregations further substantiate the genetic basis for Phytophthora resistance in Catharanthus. In combination, Tables 5–7 further demonstrate the genetic basis for the resistance gene as a single dominant allele.

TABLE 6

$F_1$ and Self Crosses Involving Resistant Phenotype Individuals

| Resistant Phenotype Individual | Female Parent | Male Parent | Cross Number | Segregating Progeny Ratio (Resistant:Sensitive) | Conclusion |
|---|---|---|---|---|---|
| 13516-2 | 13516-2 × | SELF = | 14602 | (3:1[a]) | 13516-2 is heterozygous, Rr |
| | 14590-9[b] × | 13516-2 = | 14800 | (1:1[a]) | " |
| | 13534-10[b] × | 13516-2 = | 14705 | (1:1[a]) | " |
| | 13522-9[b] × | 13516-2 = | 14712 | (1:1[a]) | " |
| 13516-8 | 13516-8 × | SELF = | 14606 | (1:0[a]) | 13516-8 is homozygous, RR |
| | 12974-5[b] × | 13516-8 = | 14662 | (1:0[a]) | " |
| | 13522-6[b] × | 13516-8 = | 14663 | (1:0[a]) | " |
| | 13533-2[b] × | 13516-8 = | 14664 | (1:0[a]) | " |
| | 13536-41[b] × | 13516-8 = | 14667 | (1:0[a]) | " |
| 13516-17 | 13516-17 × | SELF = | 14605 | (3:1[c]) | 13516-17 is heterozygous, Rr |
| | 13522-6[b] × | 13516-17 = | 14669 | (1:1[a]) | " |
| 13516-17 (cont'd) | 13534-26[b] × | 13516-17 = | 14671 | (1:1[a]) | " |
| | 13535-50[b] × | 13516-17 = | 14672 | (1:1[a]) | " |
| | 13536-41[b] × | 13516-17 = | 14673 | (1:1[a]) | " |
| | 13534-6[b] × | 13516-17 = | 14703 | (1:1[a]) | " |
| | 13516-17 × | 13500-18[b] = | 14711 | (1:1[a]) | " |
| | 13861-1[b] × | 13516-17 = | 14790 | (1:1[a]) | 13516-17 is heterozygous Rr |
| | 13043-3[b] × | 13516-17 = | 14844 | (1:1[a]) | " |
| 13518-43 | 13518-43 × | SELF = | 14912 | (3:1[a]) | 13518-43 is heterozygous, Rr |
| | 14322-39[b] × | 13518-43 = | 15060 | (1:1[a]) | " |
| 13518-49 | 13518-49 × | SELF = | 14900 | (3:1[a]) | 13518-49 is heterozygous, Rr |
| | 14322-18[b] × | 13518-49 = | 15038 | (1:1[a]) | " |
| | 13518-49 × | 13500-11[b] = | 15224 | (1:1[a]) | " |
| | 13518-49 × | 13509-1[b] = | 15226 | (1:1[a]) | " |
| 13518-59 | 13518-59 × | SELF = | 14919 | (1:0[a]) | 13518-59 is homozygous, RR |
| | 14322-46[b] × | 13518-59 = | 15064 | (1:0[a]) | " |
| | 14322-1[b] × | 13518-59 = | 15065 | (1:0[a]) | " |
| | 14322-36[b] × | 13518-59 = | 15385 | (1:0[a]) | " |
| 13518-63 | 13518-63 × | SELF = | 14919 | (1:0[a]) | 13518-63 is homozygous, RR |
| | 14322-23[b] × | 13518-63 = | 15039 | (1:0[a]) | " |
| | 13639-3[b] × | 13518-63 = | 15040 | (1:0[c]) | " |
| 13518-69 | 13518-69 × | SELF = | 14902 | (3:1[a]) | 13518-69 is heterozygous, Rr |
| | 14322-12[b] × | 13518-69 = | 15042 | (1:1[c]) | " |
| | 13518-69 × | 13498-3[b] = | 15227 | (1:1[a]) | " |
| | 13518-69 × | 13500-11[b] = | 15228 | (1:1[a]) | " |
| | 13518-69 × | 13509-1[b] = | 15229 | (1:1[a]) | " |

[a] Significant ratio based on Chi Square, P < .05.
[b] Known to be sensitive, from a background that has never segregated any resistance, see Table 1.
[c] Sample size too small for significance test.

TABLE 7

$F_2$ Phenotypic Segregation for Resistance in Lines Derived from Populations 13516, 13517, and 13518.

| | | |
|---|---|---|
| 14590-9[b] × 13516-2[a] = | 14800 progeny segregated 1:1 (RES:SEN), SEN progeny discarded; RES progeny selfed for $F_2$ | $F_2$ = 15808 expected 3:1 (RES:SEN) observed 3:1 (72:21), significant at p <<.05 |
| 13522-6[b] × 13516-17[a] = | 14669 progeny segregated 1:1 (RES:SEN), SEN progeny discarded; RES progeny selfed for $F_2$ | $F_2$ = 15770 expected 3:1 (RES:SEN) observed 3:1 (126:32), significant at p <<.05 |
| 13533-2[b] × 13516-8[a] = | 14664 progeny segregated 1:0 (RES:SEN), RES progeny selfed for $F_2$ | $F_2$ = 15795 expected 3:1 (RES:SEN) observed 3:1 (216:70), significant at p <<.05 |

[a] See Table 6 for determination of genotype.
[b] Known to be sensitive, from a background that never segregates resistance, see Table 1.

Example 7

Phytophthora Resistant Open—Pollinated Cultivars

As previously discussed, all existing commercial periwinkle cultivars are produced as open-pollinated crops. Flowers are primarily self pollinated in production fields or greenhouses and the resulting seed is harvested and sold. Open pollinated crops, including periwinkle, must be true breeding (homozygous) for desirable traits in order for expression of uniform continuity. Homozygous resistant (RR) lines have been developed which segregate only the resistant phenotype in all succeeding open-pollinated generations. The homozygous resistant lines now incorporate other homozygous horticulturally desirable traits including, but not limited to, plant habit, flower colors and flower size. Using conventional cross breeding methods, we have now crossed the Phytophthora resistance gene into all of the commercially significant periwinkle cultivars listed in Table 1 including the "Little", "Cooler", "Pretty In", and "Tropicana" series. Both the expression and segregation of the resistance gene in these diverse backgrounds were transferred as we had expected. This broad genetic base was used in the development of new Phytophthora resistant cultivars.

Example 8

Phytophthora Resistant $F_1$ Hybrid Cultivars

Even though all currently available commercial periwinkle cultivars are produced as open-pollinated crops, Phytophthora resistant $F_1$ hybrids also can be produced. In $F_1$ hybrids, a female line, incapable of pollinating itself either because it lacks pollen or is manually emasculated, is pollinated with pollen from another pollen-producing ("male") line. The resulting $F_1$ hybrid benefits from hybrid vigor and expresses aspects of both the pollen parent and female genomes. Other than periwinkle, a very large proportion of both the flower and vegetable seed, now sold is $F_1$ hybrid seed.

Periwinkle lines have been produced which are suitable for use as females in $F_1$ hybrid seed production. Because Phytophthora resistance is monogenically controlled by a dominant allele, either the male, female or both can provide Phytophthora resistance which will be expressed in the $F_1$ hybrid generations. Such a production scheme has resulted in new $F_1$ hybrid cultivars that are uniformly Phytophthora resistant.

Example 9

Additional Resistance to Other Pests including Aphids and Mites

Long term breeding programs for development of new periwinkle cultivars have provided ample opportunity to observe performance of existing cultivars and breeding lines with respect to sensitivity to common greenhouse pests including aphids (*Myzus persicae*) and mites (*Tetranychus urticae*). Table 8 indicates qualitative differences in susceptibility of selected lines and cultivars to these common greenhouse pests. Interestingly, lines selected for resistance to Phytophthora are less prone to attack by greenhouse pests such as aphids and inites. Conversely, lines known to be Phytophthora sensitive, are more prone to attack by aphids and mites. As shown in Table 8, line 13812 which was selected for extreme Phytophthora sensitivity is also extremely prone to aphid and mite infestations. Expression of the Phytophthora resistance gene of the instant invention appears to be strongly correlated with enhanced protection from other pests including, but not limited to, aphids and mites.

TABLE 8

Comparative[a] Mite and Aphid Resistance in Selected Catharanthus Cultivars and Breeding Lines[b]

| Cultivar or Line Number | Phytophthora Resistant | Aphid Resistance Level[c] | Mite Resistance Level[c] |
|---|---|---|---|
| 13500 | No | Average | – |
| 14322 | No | Average | Average |
| 13812 | No | — | — |
| 15620 | Yes | Average | + |
| 8941 | Yes | ++ | ++ |
| 15667 | Yes | ++ | ++ |

[a] Based on visual observations of plants grown in controlled greenhouse environment.
[b] See Table 9 for description of line numbers.
[c] — is very sensitive, – is sensitive, + is somewhat resistant, ++ is very resistant.

Example 10

Evaluation of Resistant Phenotypes—Possible Mechanism(s) of Action

As discussed prevously, Catharanthus species are well known for their production of alkaloids. Table 9 indicates the relationship between total alkaloid content and expression of Phytophthora resistance in selected Catharanthus lines. Line 15667, selected for Phytophthora resistance, contains more than 3.6 times the consensus level of total alkaloids reported for any other Catharanthus species or cultivar. Line 15667 is also highly resistant to aphids and mites as shown in Table 8. Indirect evidence thus indicates that the mode of action of the Phytophthora resistance gene involves enhanced alkaloid production and/or activity. Other lines such as 15614 and 15620 in Table 9, do not have elevated total alkaloid levels, yet still express Phytophthora resistance, thus suggesting that qualitative changes in alkaloid composition, rather than total alkaloid content, may have effected the resistance phenotype, The Phytophthora resistance gene of the instant invention is strongly implicated in the modulation of alkaloid synthesis and activity in Catharanthus. This activity, however, does not preclude other possible aspects of the resistance phenomenon.

Example 11

Transformation of Other Crop Species with the Resistance Gene to Provide Pest Resistance The direct applicability of using the Phytophthora resistance gene of the present invention in transformation of other crops species sensitive to Phytophthora diseases is significant. Transformation methods now applied to many plant species (cf. Robinson and Riroozabady, Scientia Horticulturae 55:83–99, 1993) enable the movement of desirable genes from a source (in this case, Phytophthora resistant Catharanthus) to a target species. Using currently available molecular methods known to those in the art, the gene is sequenced, cloned and inserted in other species where its expression is valuable. Expression of the resistance gene in crops now sensitive to aerial Phytophthora diseases including palms, Bougainvillea and other ornamentals provide a new source of non-pesticide protection. At first glance, one might suspect that heightened alkaloid levels (and thus Phytophthora resistance) might interfere with food crops. While this situation is possible, potatoes provide a good example of how food crops will benefit from transformational insertion of our resistance gene; potato stems and leaves are already toxic due to high levels of alkaloids they contain, yet tubers produced by the plants are edible. Thus, altered alkaloid expression, accomplished through transformation with the resistance gene of the present invention may impart additional non-pesticide crop protection without affecting the food quality of the crop.

Selected genes have now been isolated and cloned from *Catharanthus roseus*. Meijer, et al., *Plant Mol. Biol.*, 22:379–383 (1993), incorporated herein by reference, isolated cytochrome P-450 cDNA clones from *C. roseus* using standard methods known to those skilled in the art. Goddijin, et al., *Plant Mol. Biol.* 22:907–912 (1993) incorporated herein by reference, isolated a tryptophan decarboxylase gene from *C. roseus*, and used this same gene as a selectable marker in Agrobacterium-mediated tobacco leaf disc transformation experiments. They were able to recover mature transformed tobacco plants expressing the Catharanthus gene. Methods are, thus, currently available to those skilled in the art, for transformations using our Phytophthora resistance gene in other crop species.

Example 12

Commercial Alkaloid Production Use of the Resistance Gene to Modulate Alkaloid Quantity and Quality Selection for resistance to Phytophthora has resulted in an increased level of alkaloids in selected lines. Importantly, however, it should be noted that these lines were not specifically selected for alkaloid content or quality. Since it is now apparent that the resistance gene directly influences the total amount of alkaloids produced, as shown in Table 9, one can intentionally select for increased alkaloid content by screening lines that contain the resistance gene. Yoder and Mahlberg *Am. J. Bot;.*, 63:1167–1173 (1976) suggested that the high concentration ("1.5% ") of indole alkaloids in leaves of *Catharanthus roseus* and the fact that they are mainly found in specialized cells indicate that the plant stores indole alkaloids constitutively and probably has already evolved mechanisms to overcome auto-intoxication. It is expected that elevated alkaloid contents can be attained which exceed those reported in Table 9; further, selection for specific alkaloids rather than total alkaloid content results in an effective means of improving alkaloid production in Catharanthus. Currently, we are not aware of any U.S. patents covering alkaloid synthesis genes in Catharanthus; additionally, the synthetic pathways leading to the significant alkaloids including catharanthine, vindoline, vinblastine and vincristine are only reported from Catharanthus. Quantitatively, Cathanthine, vindoline and anhydrovinblastine are the alkaloids in greatest abundance in Catharanthus as discussed in Balsevich and Hogge, *J. Nat. Prod.* 51: 1173–1177. Field grown plants of Catharanthus roseus are the only commercial soume (at present) for the production of anti-cancer therapeutic alkaloids vinblastine and vincristine. Given the dollar value of periwinkle alkaloids, even small improvements in alkaloid quantity or quality can translate to enormous economic potential. Over a long period of time, numerous attempts have been made to use tissue culture methods for in vitro production of alkaloids. Economic efficiency of these in vitro methods has not been achieved, in part due to the low amounts of alkaloids produced. Use of the Phytophthora resistance gene to increase levels of alkaloid production and/or quality can make in vitro alkaloid production feasible. For this reason, the resistance gene can be used in whole plants, plant organs, tissues, cells, protoplasts or cell extracts for any aspect of Catharanthus alkaloid production. Plants containing the genetic resistance allele of the present invention are grown under field production conditions to obtain the desired alkaloid production.

TABLE 9

Total Alkaloid Content[a] (as percent of total dry weight) of Selected Catharanthus Lines and Cultivars

| Line Number | Alkaloid Content (%) | Line Description |
|---|---|---|
| — | 0.37[b] | *Catharanthus roseus*, average of five leaf samples as reported in Farnsworth, Lloydia 24:105–139 (1961) |
| — | 1.5[b] | *Catharanthus roseus*, as reported in Yoder and Mahlberg, Am. J. Bot., 63:1167–1173 (1976) |
| — | 0.57[b] | *Catharanthus roseus*, as reported in Jones (1976), U.S. Pat. No. 3,932,417. |
| — | 1.98[b] | *Catharanthus roseus*, as reported in vanDam, Oecologia 95:425–430 (1993) |
| 13500 | 1.48 | Commercial Cultivar "Morning Mist" |
| 14322 | 1.70 | Goldsmith line, sensitive to Phytophthora |
| 13812 | 0.69 | Goldsmith line, selected for extreme sensitivity to Phytophthora |
| 15614[c] | 1.72 | Goldsmith line, selected for resistance to Phytophthora |
| 15620[c] | 1.71 | Goldsmith line, selected for resistance to Phytophthora |
| 15655[c] | 2.70 | Goldsmith line, selected for resistance to Phytophthora |
| 15667[c] | 6.26 | Goldsmith line, selected for resistance to Phytophthora |

[a]See footnote on page w.
[b]See footnote on page w.
[c]See footnote on page w.
[a]Leaf samples were taken from eight field-grown plants; extractions and analyses performed by Centre Analytical Labs, Inc., State College, PA. Extractions performed using a method based on Endo et al., Planta Medica, 53:479–482 (1987) incorporated herein by reference. Dried leaf material was ground and extracted with a suitable solvent (such as methanol), the solvent was taken to dryness, the residue re-extracted with dilute acid, the solution adjusted to pH 10, then phase partitioned with a siutable solvent (such as ethyl acetate). The solvent fraction was then evaporated yielding to total alkaloid sample.
[b]As noted by Fransworth, Lloydia, 24:105–139 (1961), total alkaloid amounts reported in the literature can be very ambiguous, due to differences in growth conditions and extraction methodologies. Jones (1976) U.S. Pat. No. 3,932,417 incorporated herein by reference, discussed, in detail, extraction methods for *Catharanthus roseus* alkaloids. The highest reported level in leaves (1.98%) is the citation indicated above. For comparative purposes, I used a consensus value of 1.7% for the total content of leaf alkaloids according to the literature for *Catharanthus roseus*.
[c]Line segregating for Phytophthora resistance; it is unknown if the plants sacrificed for sampling were phenotypically resistant or sensitive.

DEPOSIT INFORMATION

Periwinkle seeds have been placed on deposit with the American Type Culture Collection (ATCC), Rockville, Md. 20852, under Deposit Accession Number 75636 on Jan. 14, 1994.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A Catharanthus seed containing a genetic resistance to Phytophthora, wherein said seed has a pedigree which includes the plant 8424-3.

2. The Catharanthus seed of claim 1, wherein said seed contains a dominant allele for resistance to *Phytophthora parasitica*.

3. A Catharanthus plant produced by growing the seed of claim 1.

4. Pollen of the plant of claim 3.

5. An ovule of the plant of claim 3.

6. A tissue culture comprising regenerable cells of the plant of claim 3, wherein said plant contains a genetic resistance to Phytophthora.

7. A method for producing $F_1$ hybrid Catharanthus seed comprising crossing a first parent Catharanthus plant with a second parent Catharanthus plant and harvesting the resultant $F_1$ hybrid Catharanthus seed, wherein said first or second parent Catharanthus plant is the Catharanthus plant of claim 3.

8. The method of claim 7, wherein said Catharanthus plant is the female plant.

9. The method of claim 7, wherein said Catharanthus plant is the male plant.

10. A first generation ($F_1$) hybrid Catharanthus plant produced by growing said hybrid Catharanthus seed of claim 7.

11. A Catharanthus plant according to claim 3, having a total alkaloid content of the leaf tissue of about 2.0% or greater.

12. A Catharanthus plant according to claim 3, wherein said total alkaloid content of the leaf tissue is between about 2.0% and about 3.0%.

13. A Catharanthus plant according to claim 3, wherein said total alkaloid content of the leaf tissue is between about 3.0% and about 4.0%.

14. A Catharanthus plant according to claim 3, wherein said total alkaloid content of the leaf tissue is between about 4.0% and about 5.0%.

15. A Catharanthus plant according to claim 3, wherein said total alkaloid content of the leaf tissue is between about 5.0% and about 6.0%.

16. A Catharanthus plant according to claim 3, wherein said total alkaloid content of the leaf tissue is between about 6.0% and about 6.5%.

17. A Catharanthus plant product derived from a substantially homogeneous assemblage of Catharanthus plants having a total alkaloid content of the leaf tissue of about 2.0% to about 6.5%, said plants having a pedigree which includes the plant 8424-3.

18. A Catharanthus plant product derived from a substantially homogeneous assemblage of Catharanthus plants according to claim 17, wherein said total alkaloid content is between about 2.0% and about 3.0%.

19. A Catharanthus plant product derived from a substantially homogeneous assemblage of Catharanthus plants according to claim 17, wherein said total alkaloid content is between about 3.0% and about 4.0%.

20. A Catharanthus plant product derived from a substantially homogeneous assemblage of Catharanthus plants according to claim 17, wherein said total alkaloid content is between about 4.0% and about 5.0%.

21. A Catharanthus plant product derived from a substantially homogeneous assemblage of Catharanthus plants according to claim 17, wherein said total alkaloid content is between about 5.0% and about 6.0%.

22. A Catharanthus plant product derived from a substantially homogeneous assemblage of Catharanthus plants according to claim 17, wherein said total alkaloid content of about 6.0% and about 6.5%.

23. A Catharanthus variety consisting of a substantially homogeneous assemblage of Catharanthus plants having a total alkaloid content of about 2.0% to about 6.5%, said plants having a pedigree which includes the plant 8424-23.

24. A Catharanthus variety consisting of a substantially homogeneous assemblage of Catharanthus plants according to claim 23, wherein said total alkaloid content is between about 2.0% and 3.0%.

25. A Catharanthus variety consisting of a substantially homogeneous assemblage of Catharanthus plants according to claim 23, wherein said total alkaloid content is between about 3.0% and 4.0%.

26. A Catharanthus variety consisting of a substantially homogeneous assemblage of Catharanthus plants according to claim 23, wherein said total alkaloid content is between about 4.0% and 5.0%.

27. A Catharanthus variety consisting of a substantially homogeneous assemblage of Catharanthus plants according to claim 23, wherein said total alkaloid content is between about 5.0% and 6.0%.

28. A Catharanthus variety consisting of a substantially homogeneous assemblage of Catharanthus plants according to claim 23, wherein said total alkaloid content is between about 6.0% and 6.5%.

29. A method for producing a periwinkle plant having a total alkaloid content of the leaf tissue of 2.0% to about 6.5% comprising the steps of:

a) planting in pollinating proximity seeds of a periwinkle genotype containing a genetic resistance to Phytophthora, wherein said seeds have a pedigree which includes the plant 8424-3, and another periwinkle genotype;

b) cultivating periwinkle plants resulting from said seeds until said plants bear flowers;

c) emasculating the male flowers of the plants of either periwinkle genotype;

d) allowing cross pollination to occur between said periwinkle genotypes;

e) harvesting seeds produced on said emasculated plants of the periwinkle line, and f) germinating said harvested seed to produce a periwinkle plant.

30. A first generation ($F_1$) hybrid periwinkle plant produced by growing said hybrid periwinkle seed of claim 29.

31. An $F_1$ hybrid periwinkle plant having a total alkaloid content of about 2.0% to about 6.5% and having a pedigree which includes the plant 8424-3.

32. An $F_1$ hybrid periwinkle plant according to claim 31, wherein said total alkaloid content is between about 2.0% and about 3.0%.

33. An $F_1$ hybrid periwinkle plant according to claim 31, wherein said total alkaloid content is between about 3.0% and about 4.0%.

34. An $F_1$ hybrid periwinkle plant according to claim 31, wherein said total alkaloid content is between about 4.0% and about 5.0%.

35. An $F_1$ hybrid periwinkle plant according to claim 31, wherein said total alkaloid content is between about 5.0% and about 6.0%.

36. An $F_1$ hybrid periwinkle plant according to claim 31, wherein said total alkaloid content is between about 6.0% and about 6.5%.

37. Viable Catharanthus seeds and plants and succeeding generations thereof grown from the seeds deposited under ATCC Accession No. 75636 and Catharanthus seeds and plants to which the Phytophthora resistance allele is transferred from said deposited seeds or succeeding generations thereof.

38. The method of developing a periwinkle plant having a total alkaloid content of 2.0% or greater, comprising crossing a first periwinkle genotype with a second periwinkle genotype, at least one of said genotypes containing a total alkaloid content of 2.0% or greater and having a pedigree which includes the plant 8424-3.

* * * * *

UNITED STATES PATENT AND TRADEMARK OFFICE
CERTIFICATE OF CORRECTION

PATENT NO. : 5,491,285
DATED : February 13, 1996
INVENTOR(S) : Robert N. BOWMAN

It is certified that error appears in the above-indentified patent and that said Letters Patent is hereby corrected as shown below:

Cover Page, left column, under PUBLICATIONS, third line, delete "Fungicid" and substitute therefor --Fungicide--.

right column, under ABSTRACT, line 5, delete "Phytophthorao" and substitute therefor-- Phytophthora--.

Column 2, line 16, delete "fungicities" and substitute therefor --fungicides--.

Column 5, line 19, delete "at." and substitute therefor --al.--.

line 53, delete "fungat" and substitute therefor --fungal--.

Column 7, line 5, delete "," and substitute therefor --.--.

Column 9, line 41, delete "geneo." and substitute therefor --gene.--.

Table 6, left column, delete "(cont'd)".

Column 13, Example 9, line 63, delete "inites." and substitute therefor --mites.--.

UNITED STATES PATENT AND TRADEMARK OFFICE
CERTIFICATE OF CORRECTION

PATENT NO. : 5,491,285
DATED : February 13, 1996
INVENTOR(S) : Robert N. BOWMAN

It is certified that error appears in the above-indentified patent and that said Letters Patent is hereby corrected as shown below:

Column 14, line 42, delete "phenotype," and substitute therefor --phenotype.--.

Column 15, line 55, delete "Cathanthine" and substitute therefor --Catharanthine--.

line 59, delete "soume" and substitute therefor --source--.

Column 16, line 35, delete "aSee footnote on page w".

Column 16, line 36, delete "bSee footnote on page w".

line 37, delete "cSee footnote on page w".

line 43, delete "to" and substitute therefor --the--.

UNITED STATES PATENT AND TRADEMARK OFFICE
CERTIFICATE OF CORRECTION

PATENT NO. : 5,491,285
DATED : February 13, 1996
INVENTOR(S) : Robert N. BOWMAN

It is certified that error appears in the above-indentified patent and that said Letters Patent is hereby corrected as shown below:

Column 17, line 67, last word, delete "of" and substitute therefor --is between--.

Column 18, line 45, delete "hybridperiwinkle" and substitute therefor --hybrid periwinkle--.

Signed and Sealed this

Twenty-seventh Day of May, 1997

Attest:

BRUCE LEHMAN

Attesting Officer

Commissioner of Patents and Trademarks